United States Patent [19]

Huth et al.

[11] Patent Number: 4,623,649
[45] Date of Patent: Nov. 18, 1986

[54] SUBSTITUTED β-CARBOLINES, AND USE THEREOF AS MEDICINAL AGENTS

[75] Inventors: Andreas Huth; Ralph Schmiechen; Dieter Rahtz; Dieter Seidelmann, all of Berlin, Fed. Rep. of Germany; Claûs T. Braestrûp, Roskilde, Denmark

[73] Assignee: Schering Aktiengesellschaft, Berlin and Bergkamen, Fed. Rep. of Germany

[21] Appl. No.: 654,594

[22] Filed: Sep. 26, 1984

[30] Foreign Application Priority Data

Sep. 27, 1983 [DE] Fed. Rep. of Germany ....... 3335323

[51] Int. Cl.⁴ ..................... A61K 31/33; C07D 471/04
[52] U.S. Cl. ..................................... 514/292; 546/85; 546/86
[58] Field of Search ..................... 546/85, 86; 514/292

[56] References Cited

U.S. PATENT DOCUMENTS

| | | | |
|---|---|---|---|
| 3,058,909 | 10/1962 | Kern | 546/86 |
| 3,163,219 | 12/1964 | Wyant et al. | 546/85 |
| 3,215,634 | 11/1965 | Walker | 546/86 |
| 3,696,035 | 10/1972 | Nimerick | 546/85 |
| 3,727,688 | 4/1973 | Clampitt | 546/86 |
| 3,741,894 | 8/1973 | Storfer | 546/86 |
| 3,768,566 | 8/1975 | Ely et al. | 546/86 |
| 3,848,673 | 11/1974 | Clampitt et al. | 546/86 |
| 3,888,312 | 6/1975 | Tiner et al. | 546/85 |
| 3,978,928 | 9/1976 | Clampitt | 546/85 |
| 4,001,210 | 1/1977 | Engelskirchen et al. | 546/85 |
| 4,013,821 | 3/1977 | Engelskirchen et al. | 546/85 |
| 4,033,415 | 7/1977 | Holtmyer et al. | 546/86 |
| 4,096,326 | 6/1978 | Reid | 546/86 |
| 4,144,179 | 3/1979 | Chatterji | 546/85 |
| 4,323,123 | 4/1982 | Swanson | 546/85 |

FOREIGN PATENT DOCUMENTS

| | | | |
|---|---|---|---|
| 0054507 | 6/1982 | European Pat. Off. | 546/85 |
| 0110813 | 6/1984 | European Pat. Off. | 546/86 |
| 0030254 | 10/1984 | European Pat. Off. | 546/86 |
| 1470396 | 11/1969 | Fed. Rep. of Germany | 546/86 |

OTHER PUBLICATIONS

The Patent Office Japanese Government "Patent Abstracts of Japan", Apr. 22, 1982, Section C, vol. 6, No. 63.

Primary Examiner—Henry R. Jiles
Assistant Examiner—J. Richter
Attorney, Agent, or Firm—Millen & White

[57] ABSTRACT

Novel substituted β-carboline derivatives of Formula I wherein
$R^3$ is an oxadiazolyl residue of the formula wherein $R^5$ stands for lower alkyl of up to 3 carbon atoms or an ester $$\overset{O}{\underset{}{\overset{\|}{C}}}-OR^6$$

with $R^6$ being hydrogen or lower alkyl of up to 3 carbon atoms,
$R^4$ is hydrogen, lower alkyl of up to 3 carbon atoms, or $CH_2OR^9$ wherein $R^9$ is lower alkyl of up to 3 carbon atoms,
$R^A$ is phenyl or a hydrocarbon residue containing 2–10 carbon atoms which can be cyclic or acyclic, saturated or unsaturated, branched or unbranched, and which can optionally be substituted by oxo, formyl OH, O-alkyl of up to 3 carbon atoms or phenyl, and wherein, in a cyclic hydrocarbon residue, a $CH_2$-group can be replaced by oxygen, exhibit an effect on the central nervous system and thus are suitable as psychopharmaceuticals.

30 Claims, No Drawings

SUBSTITUTED β-CARBOLINES, AND USE THEREOF AS MEDICINAL AGENTS

The present invention relates to novel substituted β-carbolines, a process for their preparation and their use as medicinal agents.

SUMMARY OF THE INVENTION

It is an object of this invention to provide new β-carbolines having valuable pharmacological properties.

Upon further study of the specification and appended claims, further objects and advantages of this invention will become apparent to those skilled in the art.

These objects have been achieved by providing new substituted β-carboline derivatives of Formula I

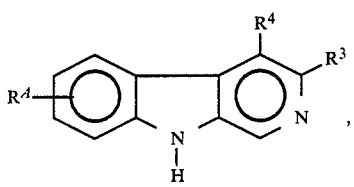

wherein
$R^3$ is an oxadiazolyl residue of the formula

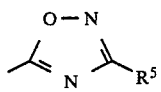

wherein $R^5$ stands for lower alkyl of up to 3 carbon atoms, or $R^3$ is an acid or ester group

with $R^6$ being hydrogen or lower alkyl of up to 3 carbon atoms, $R^4$ is hydrogen, lower alkyl of up to 3 carbon atoms, or $-CH_2OR^9$ wherein $R^9$ is lower alkyl of up to 3 carbon atoms, and $R^A$ is a phenyl or a hydrocarbon residue containing 2-10 carbon atoms which can be cyclic or acyclic, saturated or unsaturated, branched or unbranched, and which can optionally be substituted by $=O$, i.e., oxo, formyl($-CHO$), OH, O-alkyl of up to 3 carbon atoms, or phenyl, and wherein, in a cyclic hydrocarbon residue, a $CH_2$- group can be replaced by oxygen, i.e., oxa.

The compounds of this invention exhibit valuable pharmacological properties. They influence, in particular, the central nervous system and are thus suitable as psychopharmaceuticals.

DETAILED DISCUSSION

The novel β-carbolines of Formula I are substituted in the 3-position by a substituted [1,2,4]oxadiazol-5-yl residue or by an alkoxycarbonyl residue, wherein the alkyl substituent on the oxadiazolyl residue and on the oxycarbonyl group is, in both cases, lower alkyl of up to 3 carbon atoms. Examples are methyl, ethyl, propyl, and isopropyl.

The novel β-carbolines are substituted in the 4-position (4-hydrogen), or are substituted by lower alkyl as above, e.g., methyl or ethyl, or by lower alkoxymethyl.

The substituent $R^A$ is a hydrocarbon residue of 2-10 carbon atoms, which residue can be cyclic or open-chained, saturated or unsaturated (alkyl, alkenyl, and their cyclic versions), branched or unbranched. Examples include cyclopentyl, cyclohexyl, cycloheptyl, cyclooctyl, 2-pentyl, n-butyl, tert-butyl, n-hexyl, 1,3-butadienyl, 1-cyclohexenyl, 4-cycloheptenyl, 1-cyclooctenyl, 2,3-dimethyl-1,3-butadienyl, 3-methyl-1,3-butadienyl, cyclohexylvinyl, 3-methylbutyl, phenethyl, 2,3-dimethylbutyl, or 2-cyclohexylethyl. In addition to these nonaromatic groups, $R^A$ can also be phenyl.

The hydrocarbon residue $R^A$ can furthermore be substituted by a phenyl group, by a hydroxy group, or by a lower alkoxy group of up to 3 carbon atoms. Moreover, a $CH_2$-group can also be replaced by a carbonyl group.

The substituent $R^A$ is generally in the 5- or 6-position, the 6-position being preferred.

Contemplated equivalents of compounds of Formula I are those novel compounds wherein alkyl portions in $R^3$ and $R^4$ are substituted and wherein hydrogen atoms are replaced, e.g., by alkyl groups, in all such cases the resultant compound being one having a spectrum of biological activity equivalent to that described herein.

It is known that certain sites in the central nervous system of vertebrates show a high specific affinity for binding 1,4- and 1,5-benzodiazepines (Squires, R. F. and Braestrup, C., Nature (London) 266 (1977) 734). The sites are called benzodiazepine receptors. It has been discovered that the substituted β-carbolines of this invention, though greatly different in their chemical structure from benzodiazepines, surprisingly exhibit a strong affinity and specificity for binding to benzodiazepine receptors, e.g., as evidenced by the fact that they displace radioactively tagged flunitrazepam from these benzodiazepine receptors.

The displacement activity of the compounds of the invention is indicated in the table below as the $IC_{50}$ and $ED_{50}$ values. The $IC_{50}$ value indicates the concentration effecting a 50% displacement of the specific binding of $^3H$ flunitrazepam (1.0 nM, 0° C.) in specimens with a total volume of 0.55 ml of a cerebral membrane suspension, for example from rats.

The displacement activity is determined by in vitro test as follows: 0.5 ml of a suspension of untreated rat cerebrum in 25 mM $KH_2PO_4$, pH=7.1 (5-10 mg of tissue/specimen) is incubated for 40-60 minutes at 0° C. together with $^3H$ diazepam (specific activity 14.4 Ci/mmol, 1.9 nM) or $^3H$ flunitrazepam (specific activity 87 Ci/mmol, 1.0 nM). After incubation, the suspension is filtered through a porous glass plate, the residue is washed twice with cold buffer solution, and the radioactivity is measured by means of a scintillation counter.

Then the test is repeated, but in such a way that, prior to adding the radioactively tagged benzodiazepine, there is introduced a certain quantity or an excess amount of the compound, the displacement activity of which is to be determined. The $IC_{50}$ value is calculated on the basis of the thus-obtained data.

The $ED_{50}$ value represents the dose of a test compound effecting a reduction of the specific binding of flunitrazepam to the benzodiazepine receptor in a living brain to 50% of the control value.

The in vivo test is performed as follows:

Groups of mice are injected with the test compound at varying doses and normally subcutaneously. After 15 minutes, the mice receive $^3H$ flunitrazepam intravenously. After another 20 minutes, the mice are sacrificed, their forebrain membranes are removed, and the radioactivity of the forebrain membranes is measured by scintillation counter. The $ED_{50}$ value is determined with the aid of the dose/effect curves.

The results of the pharmacological tests are compiled in the following table.

TABLE

Displacement Activity of Substituted β-Carboline Derivatives of Formula I

| Substituent | | $R^A$ | | $IC_{50}$ ng/ml | $ED_{50}$ mg/ml |
|---|---|---|---|---|---|
| $R^3$ | $R^4$ | 5-position | 6-position | (in vitro) | (in vivo) |
| $CO_2Me$ | H | H | H* | 1.9 | 22 |
| $CO_2Et$ | Me | H | cyclohexyl | 12 | 4.7 |
| $CO_2Et$ | Me | H | $-C(CH_3)_3$ | 7.5 | 3.3 |
| $CO_2Et$ | Me | H | $-CH_2-CH_2-C_6H_5$ | 14 | 11 |
| $CO_2Et$ | Me | H | cyclooctyl | 19 | 11 |
| $CO_2Et$ | $CH_2OCH_3$ | H | cyclohexenyl mixture 1:4 | 0.7 | 0.5 |
| O—N / N—Et (oxadiazole-Et) | $CH_2OCH_3$ | H | cyclohexenyl mixture 1:4 | 1.5 | 1.9 |
| $CO_2Et$ | H | H | $-CH(CH_3)_2$ | 0.9 | 3.7 |
| $CO_2Et$ | $CH_2OCH_3$ | $CH_2-C_6H_5$ | H | 0.5 | 3.5 |
| $CO_2Et$ | Me | H | cyclohexanone | 0.6 | 0.9 |

*Nature 294(1981)472

The compounds of this invention are suitable, based on their biological efficacy, as psychopharmaceuticals for human medicine. In this connection, they can be utilized as formulated into pharmaceutical preparations, for example for oral and parenteral administration.

Suitable formulating aids are physiologically compatible, organic and inorganic excipients inert with respect to the compounds of this invention. Examples for excipients include water, salt solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, polyvinylpyrrolidone, etc.

The pharmaceutical preparations can be sterilized and/or combined with auxiliary agents, such as lubricants, preservatives, stabilizers, wetting agents, emulsifiers, buffers, and colorants. Especially suitable for parenteral administration are injection solutions or suspensions, particularly aqueous solutions of the active compounds in polyhydroxyethoxylated castor oil. For oral administration, particularly suited are tablets, dragees, or capsules with talc and/or a hydrocarbon excipient or binder, e.g. lactose, cornstarch, or potato starch. The formulations can also be in liquid form, for example as an elixir to which a sweetener is added, if desired.

The compounds of this invention are generally incorporated into a physiologically compatible excipient in a dosage unit of 0.05-10 mg of active ingredient. They generally are utilized in a dosage from 0.1 to 300 mg/day, preferably 1-30 mg/day.

All compounds of this invention have affinity for benzodiazepine receptors. Consequently, they have a spectrum of the activities of the benzodiazepines, e.g., muscle relaxant, sedative, anxiolytic or anticonvulsant and are useful for the conventional corresponding indications, e.g., as muscle relaxants, antiepileptics, sedatives, hypnotic, tranquilizers, etc. These activities can be from agonistic to antagonistic to inverse agonistic, the corresponding indications being conventional in each case, e.g., antagonistically they can be used to reverse benzodiazepine effects, e.g., in cases of overdose, inverse agonistically they can be used to achieve the inverse effects of the benzodiazepines, e.g., they can be used as vigilance enhancers, etc. The type and level of activity for a given dosage of each compound can be conventionally determined by routine experimentation using well known pharmacological protocols for each of the activities; the corresponding indications treatable at that dosage will be well known to skilled workers based on the pharmacological results.

The compounds of this invention are particularly noteworthy for their anticonvulsant and anxiolytic activity, e.g., to treat epilepsy and anxiety, each at dosages of 1 to 30 mg/day, analogously to the known agent diazepam.

The compounds of this invention according to Formula I can be produced according to methods known per se. For example:

A. A halogenated β-carboline derivative of Formula II

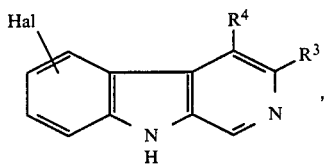

wherein

Hal is bromine or iodine and $R^3$ and $R^4$ are as defined above, can be alkenylated with an unsaturated hydrocarbon in an aprotic polar solvent in the presence of a heavy metal salt and a base under pressure. Subsequently, optionally, the isolated or conjugated double bond present in substituent $R^4$ can be hydrogenated in a protonic solvent in the presence of Raney nickel or a noble metal catalyst on a support material, or can be subsequently dehydrogenated with elemental sulfur in dimethyl sulfoxide or with palladium in xylene and/or mesitylene, and subsequently, optionally, an ester group in the 3-position can be subjected to alkaline hydrolysis and, optionally, thereafter the thus-obtained free acid of Formula III

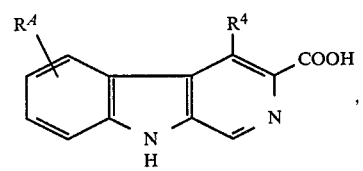

wherein $R^4$ and $R^A$ are as defined above, can be reacted with an amidoxime of the formula $R^5$—C(=NOH)NH$_2$ wherein $R^5$ is as defined above, in an inert solvent at room temperature up to the boiling temperature of the reaction mixture.

B. A β-carboline derivative of Formula IV

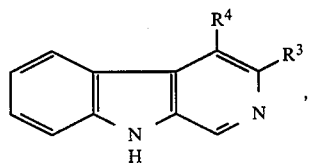

wherein $R^3$ and $R^4$ are as defined above, can be alkylated at room temperature with an alkyl halogenide or an alkene of 2-10 carbon atoms, the halogenide being chlorine or bromine, in the presence of aluminum trichloride.

C. A substituted β-carboline derivative of Formula V

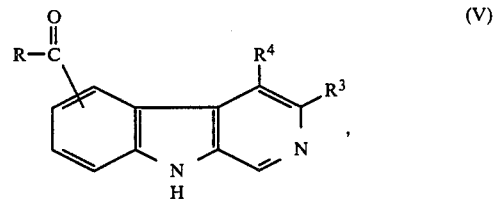

wherein

R is a hydrogen or a hydrocarbon residue of up to 9 carbon atoms and $R^3$ and $R^4$ are as defined above, can be hydrogenated in the presence of palladium in finely divided form in an aliphatic alcohol and glacial acetic acid at temperatures of between 20° and 100° C. and under pressures of 5–20 bar.

D. A substituted indole of Formula VI

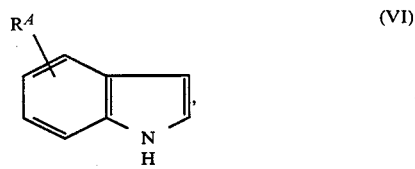

wherein $R^A$ is as defined above, can be reacted with an azadiene of Formula VII

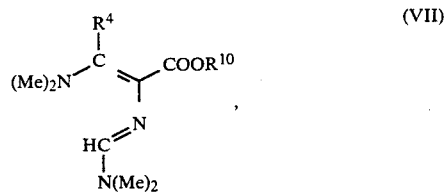

wherein $R^4$ is as defined above, and $R^{10}$ is a lower alkyl residue of up to 3 carbon atoms, in the presence of an acid at temperatures of 50°–200° C.

E. A substituted indole of Formula VI can be heated with a 4-alkoxy-3-hydroxy-2-nitrobutyric acid alkyl ester of Formula VIII

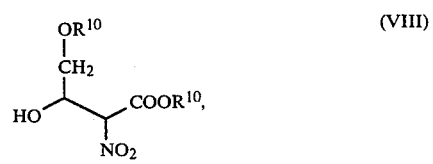

wherein $R^{10}$ is as defined above, in an inert solvent at the reflux temperature in the presence of an aliphatic carboxylic acid, whereafter, the thus-obtained 3-(4-alkoxyindol-3-yl)-2-nitro-5-oxahexanoic alkyl ester of Formula IX

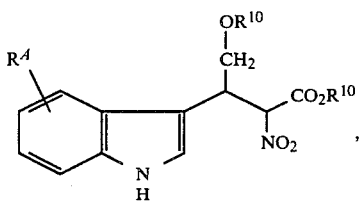

(IX)

wherein $R^4$ and $R^{10}$ is as defined above, is hydrogenated to the corresponding 2-amine compound in the presence of Raney nickel at room temperature and under normal pressure, reacted with glyoxylic acid at a pH of 3–5 at room temperature, thus obtaining an $R^4$-substituted 4-alkoxymethyl-1,2,3,4-tetrahydro-$\beta$-carboline-1-carboxylic acid-3-carboxylic acid alkyl ester of Formula X

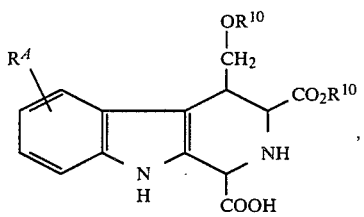

(X)

wherein $R^{10}$ and $R^4$ are as defined above, and this ester being subsequently decarboxylated in a high-boiling inert solvent by heating to the reflux temperature and thereafter being dehydrogenated.

In order to produce compounds of Formula I wherein $R^4$ is an unsaturated hydrocarbon residue of 2–10 carbon atoms, which can be cyclic or acyclic, branched or straight-chained, and can be substituted with oxygen, hydroxy, alkoxy of up to 3 carbon atoms, and phenyl as the substituents, a $\beta$-carboline of Formula II, substituted in the A-ring of the $\beta$-carboline molecule by halogen, such as bromine or iodine, can be reacted under pressure with an unsaturated hydrocarbon, as defined hereinabove as a residue, in an aprotic polar solvent in the presence of a heavy metal salt and a base.

Examples of aprotic polar solvents include dimethylformamide, methylpyrrolidone, hexamethylphosphoric triamide, dimethylacetamide, acetonitrile, and trimethylene glycol dimethyl ether. Especially suitable as the heavy metal salts are the usual chlorides, sulfates, and acetates of ruthenium, rhodium, palladium, and platinum, together with organic phosphorus compounds, such as triphenylphosphine and tri-o-tolylphosphine. Suitable as bases are actually all organic and inorganic bases, though tert-butylamine and sodium bicarbonate, for example, proved to be well suitable.

The reaction is advantageously carried out in an inert atmosphere, such as nitrogen or a noble gas, at temperatures of 70°–150° C. under a pressure in the range of 1–5 atmospheres gauge.

The optionally following hydrogenation, causing reaction of isolated and conjugated double bonds and triple bonds, but not aromatic double bonds, yields compounds of Formula I wherein the substituent $R^4$ is saturated. For this purpose, the starting material is hydrogenated in a protonic solvent, e.g., in an aliphatic alcohol, such as methanol or ethanol, in the presence of Raney nickel or a noble metal catalyst on a suitable support material, such as palladium on carbon. Suitably, hydrogenation is performed under a pressure in the range from 1–20 bar, preferably 5–10 bar.

The optionally subsequently performed dehydrogenation of substituents $R^4$ exhibiting an isolated or conjugated double bond yields compounds wherein $R^4$ represents an aromatic residue, such as the phenyl group. For this purpose, the starting material is treated either in dimethyl sulfoxide with elemental sulfur or in xylene or mesitylene or a mixture thereof with palladium on carbon while heating to 150°–200° C.

The optionally followed saponification of an ester group in the 3-position takes place suitably in an alkaline reaction wherein the ester is heated to temperatures up to the reflux temperature of the reaction mixture with dilute aqueous alkaline solution, such as potassium or sodium hydroxide, in a protonic solvent, e.g. methanol, ethanol, or ethylene glycol.

The free $\beta$-carboline-3-carboxylic acid of Formula III thus obtained as a precursor serves for producing compounds of Formula I wherein $R^3$ represents the 5-oxadiazolyl residue. For this purpose, the $\beta$-carboline-3-carboxylic acid is made to condense with an amidoxime of the formula $R^5$—C(=NOH)NH$_2$ wherein $R^5$ is a lower alkyl residue in a solvent boiling above 100° C. and inert with respect to the reactants, at the reflux temperature of the reaction mixture. Suitable solvents for the condensation reaction include, for example, toluene and dimethylformamide. Advantageously, the free $\beta$-carboline-3-carboxylic acid is suitably activated before the condensation reaction. For this purpose, the free acid can be converted into the mixed anhydride, into the activated ester, or into the chloride. Activation with imidazole/thionyl chloride in an aprotic solvent, such as dioxane, tetrahydrofuran, dimethylformamide, or N-methylpyrrolidone proved advantageous, at temperatures of between 0° and 50° C., preferably room temperature.

Another suitable technique for preparing compounds of Formula I is alkylation in the manner of a Friedel-Crafts reaction. For this purpose, the corresponding alkyl chloride is used to treat the $\beta$-carboline, unsubstituted in the A-ring, at room temperature in the presence of aluminum trichloride, thus obtaining, besides monoalkylated final products, also simultaneously dialkylated end products, for example in the 6- and 8-positions, but these can readily be separated, for example by recrystallization.

Another synthesis possibility for producing compounds of Formula I wherein $R^4$ stands for an alkyl residue is reduction of a keto or aldehyde function on the A-ring of the $\beta$-carboline molecule. For this purpose, a $\beta$-carboline derivative of Formula V is hydrogenated in the presence of palladium in finely divided form, e.g., as palladium black, in an aliphatic alcohol such as methanol or ethanol and an aliphatic carboxylic acid, such as acetic acid, under a pressure in the range of 4–20 bar at temperatures between room temperature and 100° C.

Another method for synthesizing compounds of Formula I resides in reacting an $R^4$-substituted indole of Formula VI with an azadiene of Formula VII. Reaction of the indole derivative with the azadiene takes place in the presence of acids at temperatures of between 50° and 200° C., preferably at 75°–150° C. The reaction is performed, for example, by heating the indole derivative of Formula VI and the, e.g., azabutadiene of Formula VII in an aliphatic carboxylic acid, such as formic acid, acetic acid, propionic acid, or trifluoroacetic acid, or in an inorganic medium, such as in phosphoric acid, polyphosphoric acid, or phosphoric oxychloride, etc. It is also possible to add inert organic solvents, such as, for example, toluene, ethyl acetate, dioxane, dimethoxyethane, acetonitrile, and others. However, the reaction can also be conducted in the presence of catalytic amounts of a mineral acid, such as sulfuric acid, hydrochloric acid, perchloric acid, etc., in one of the aforementioned inert solvents. The reaction is completed after 3-10 hours. The progression of the reaction can be controlled, for example, by thin-layer chromatography.

Another synthesis alternative for preparing compounds of Formula I from $R^4$-substituted indole derivatives of Formula VI is the reaction with a 4-alkoxy-3-hydroxy-2-nitrobutyric acid alkyl ester of Formula VIII. For this purpose, the reactants are heated to reflux temperature in an inert solvent, such as benzene, toluene, or xylene in the presence of an aliphatic carboxylic acid, such as acetic acid. This reaction is suitably carried out under a protective gas atmosphere. The resultant reaction product, the 3-(4-alkoxyindol-3-yl)-2-nitro-5-oxahexanoic alkyl ester of the Formula IX is hydrogenated at room temperature and under normal pressure with Raney nickel in a protonic solvent, such as methanol or ethanol. The 2-amino compound obtained during this hydrogenation is subsequently reacted with glyoxylic acid at room temperature and a pH value of 3-5, set, for example, by an aqueous potassium carbonate solution. The thus-obtained $R^4$-substituted 4-alkoxymethyl-1,2,3,4-tetrahydro-$\beta$-carboline-1-carboxylic acid-3-carboxylic acid alkyl ester of Formula X is decarboxylated in a high-boiling inert solvent, such as xylene or mesitylene under boiling heat, and then dehydrogenated.

One dehydrogenation method resides in dissolving or suspending the starting material in an inert solvent and then adding elemental sulfur, the amount of which is dimensioned approximately so that, per double bond, one molar equivalent of sulfur is utilized. A small excess is advantageous. Suitable as inert solvents are actually all aprotic solvents the boiling point of which is above 100° C. and which are inert with respect to the starting material. Examples are xylene, dioxane, tetrahydrofuran, methylene chloride, or dimethoxyethane, at temperatures of between 0° and 60° C. with reaction periods of 0.5-4 hours.

The reaction mixture is worked up in the respective processes according to generally known methods, such as extraction, crystallization, chromatography, etc.

In all of the foregoing methods, the starting material compounds are known and/or readily preparable using known methods from known or readily conventionally preparable starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples all temperatures are set forth uncorrected in degrees Celsius; unless otherwise indicated, all parts and percentages are by weight.

EXAMPLE 1

1.9 g (5 millimoles) of 6-iodo-4-methyl-$\beta$-carboline-3-carboxylic acid ethyl ester is combined in 30 ml of dimethylformamide with 0.87 ml of triethylamine, 22 mg of palladium(II) acetate, 152 mg of tri-orthotolylphosphine, and 6 ml of cyclohexene and stirred in a pressure vessel under argon for 6 hours at a bath temperature of 140° C. After the solvent has been removed by distillation, the mixture is distributed in ethyl acetate/saturated sodium bicarbonate solution and suctioned off from the insoluble proportion. The ethyl acetate phase is washed with water, dried, filtered, and concentrated. The residue is chromatographed over silica gel with toluene: glacial acetic acid:water=10:10:1 as the eluent. The corresponding fractions are concentrated, taken up in methylene chloride, washed respectively once with sodium bicarbonate solution and with saturated sodium chloride solution dried, filtered, and concentrated, thus obtaining 500 mg (38% of theory) of 6-(1-cyclohexen-4-yl)-4-methyl-$\beta$-carboline-3-carboxylic acid ethyl ester, mp 200°-201° C.

The following compounds are prepared analogously:

4-methyl-6-(1-cycloocten-1-yl)-$\beta$-carboline-3-carboxylic acid ethyl ester, mp 196°-199° C.;

a mixture of 4-methyl-6-(3- and 4-cyclohepten-1-yl)-$\beta$-carboline-3-carboxylic acid ethyl ester, mp 193° C.;

4-methyl-6-(3-methyl-1,3-butadienyl)-$\beta$-carboline-3-carboxylic acid ethyl ester, mp 198°-200° C.;

4-methyl-6-(2,3-dimethyl-1,3-butadienyl)-$\beta$-carboline-3-carboxylic acid ethyl ester;

a mixture of 5-(1- and 2-cyclohexen-4-yl)-$\beta$-carboline-3-carboxylic acid ethyl ester, mp 238°-243° C.;

a mixture of 4-ethyl-6-(1- and 2-cyclohexen 4-yl)-$\beta$-carboline-3-carboxylic acid ethyl ester;

4-ethyl-6-(1-cycloocten-1-yl)-$\beta$-carboline-3-carboxylic acid ethyl ester;

a mixture of 6-(1- and 2-cyclohexen-4-yl)-$\beta$-carboline-3-carboxylic acid ethyl ester;

6-(1-cycloocten-1-yl)-$\beta$-carboline-3-carboxylic acid ethyl ester;

a mixture of 4-methoxymethyl-6-(1- and 2-cyclohexen-4-yl)-$\beta$-carboline-3-carboxylic acid ethyl ester, mp 152°-156° C.;

4-methoxymethyl-6-(3-methyl-1,3-butadienyl)-$\beta$-carboline-3-carboxylic acid ethyl ester;

4-methyl-6-(1-cyclohexen-4-yl)-$\beta$-carboline-3-carboxylic acid ethyl ester;

4-methyl-6-(1-cyclohexen-4-yl)-$\beta$-carboline-3-carboxylic acid propyl ester;

a mixture of 4-methyl-6-(1-propyl-1- and -2-penten-1-yl)-$\beta$-carboline-3-carboxylic acid ethyl ester, mp 142°-144° C.; and 6-(cyclohexylvinyl)-4-methyl-$\beta$-carboline-3-carboxylic acid ethyl ester, mp 186°-205° C.

EXAMPLE 2

440 mg (1.31 mmol) of 6-(1-cyclohexen-4-yl)-4-methyl-$\beta$-carboline-3-carboxylic acid ethyl ester is heated under reflux for one hour in 20 ml of ethanol with 3.25 ml of 1N potassium hydroxide solution. After neutralizing with acetic acid and addition of 10 ml of water, the precipitated product is suctioned off, washed with water, and dried under vacuum over potassium hydroxide, thus obtaining 378 mg (94% of theory) of 6-(1-cyclohexen-4-yl)-4-methyl-$\beta$-carboline-3-carboxylic acid, mp 284°-285° C.

The following compounds are prepared in analogous fashion:

6-cyclohexyl-4-methyl-$\beta$-carboline-3-carboxylic acid;

6-(1-cycloocten-1-yl)-4-methyl-$\beta$-carboline-3-carboxylic acid;

6-(3-methylbut-1-yl)-4-methyl-β-carboline-3-carboxylic acid;

a mixture of 6-(1- and 2-cyclohexen-4-yl)-4-methoxymethyl-β-carboline-3-carboxylic acid, mp 240°–244° C.; and 6-tert-butyl-4-methyl-β-carboline-3-carboxylic acid.

EXAMPLE 3

1.36 g (20 mmol) of imidazole is combined in 15 ml of absolute tetrahydrofuran with 0.36 ml of thionyl chloride in 5 ml of absolute tetrahydrofuran. After 15 minutes of agitation at room temperature, the mixture is suctioned off from the precipitate. The filtrate is added to a solution of 0.33 g (1.08 mmol) of 6-(1-cyclohexen-4-yl)-4-methyl-β-carboline-3-carboxylic acid in 15 ml of absolute dimethylformamide. After agitation for one hour at room temperature, the mixture is combined with 1.15 g (13 mmol) of propionamidoxime, the tetrahydrofuran is distilled off, and the reaction solution is heated for 3 hours under reflux. After the solvent has been removed by distillation, the mixture is distributed in methylene chloride/saturated sodium bicarbonate solution, the organic phase is washed with saturated sodium chloride solution until it is neutral, dried over magnesium sulfate, filtered, and concentrated to dryness. After column chromatography over silica gel with methylene chloride:ethanol = 10:1 as the eluent, and recrystallization from ethanol/hexane, the residue yields 194 mg (50% of theory) of 6-(1-cyclohexen-4-yl)-4-methyl-3-(3-ethyl-1,2,4-oxadiazol-5-yl)-β-carboline, mp 247°–248° C.

The following compounds are prepared analogously:

6-cyclohexyl-4-methyl-3-(3-ethyl-1,2,4-oxadiazol-5-yl)-β-carboline;

a mixture of 6-(1- and 2-cyclohexen-4-yl)-4-methyl-3-(3-ethyl-1,2,4-oxadiazol-5-yl)-β-carboline;

6-(1-cycloocten-1-yl)-4-methyl-3-(3-ethyl-1,2,4-oxadiazol-5-yl)-β-carboline;

6-(3-methylbut-1-yl)-4-methyl-3-(3-ethyl-1,2,4-oxadiazol-5-yl)-β-carboline;

a mixture of 6-(1- and 2-cyclohexen-4-yl)-4-methoxymethyl-3-(3-ethyl-1,2,4-oxadiazol-5-yl)-β-carboline, mp 142°–145° C.; and 6-tert-butyl-4-methyl-3-(3-ethyl-1,2,4-oxadiazol-5-yl)-β-carboline.

EXAMPLE 4

100 mg (0.3 mmol) of 6-(1-cyclohexen-4-yl)-4-methyl-β-carboline-3-carboxylic acid ethyl ester is hydrogenated in 20 ml of ethanol with 0.1 g of Raney nickel at room temperature for 2 hours under 10 bar. After separating from the catalyst, the product is evaporated and reprecipitated from a small amount of ethanol/hexane, thus obtaining 55 mg (54.7% of theory) of 6-cyclohexyl-4-methyl-3-β-carboline carboxylic acid ethyl ester, mp 191°–193° C.

The following compounds are produced in analogy to the above:

6-cycloheptyl-4-methyl-β-carboline-3-carboxylic acid ethyl ester;

6-cyclooctyl-4-methyl-β-carboline-3-carboxylic acid ethyl ester;

6-(3-methylbut-1-yl)-4-methyl-β-carboline-3-carboxylic acid ethyl ester, mp 202°–203° C.;

6-phenethyl-4-methyl-β-carboline-3-carboxylic acid ethyl ester, mp 161°–169° C.;

6-(2,3-dimethylbutyl)-4-methyl-β-carboline-3-carboxylic acid ethyl ester;

6-cyclohexyl-4-methoxymethyl-β-carboline-3-carboxylic acid ethyl ester;

5-cyclohexyl-β-carboline-3-carboxylic acid ethyl ester, mp 254°–266° C.;

6-(1-propyl-1-pentyl)-4-methyl-β-carboline-3-carboxylic acid ethyl ester; and 6-(2-cyclohexylethyl)-4-methyl-β-carboline-3-carboxylic acid ethyl ester, mp 225°–228° C.

EXAMPLE 5

500 mg of 6-acetyl-4-methyl-β-carboline-3-carboxylic acid ethyl ester is hydrogenated at 10 bar and 70° C. for 4 hours in 90 ml of ethanol and 10 ml of glacial acetic acid with 300 mg of palladium black. After removing the catalyst by filtration, the reaction mixture is evaporated, distributed in ethyl acetate/saturated sodium bicarbonate solution, and the organic phase is dried, filtered, and concentrated. Chromatography over silica gel with methylene chloride:ethanol = 10:1 as the eluent and recrystallization of the corresponding fractions from alcohol/ethyl acetate/hexane yield 170 mg (40% of theory) of 6-ethyl-4-methyl-β-carboline-3-carboxylic acid ethyl ester, mp 158°–163° C.

EXAMPLE 6

435 mg (1.3 mmol) of 6-(1-cyclohexen-4-yl)-4-methyl-β-carboline-3-carboxylic acid ethyl ester is heated in 10 ml of dimethyl sulfoxide with 125 mg of sulfur under nitrogen for 2 hours to 180° C. After evaporation under vacuum, the reaction mixture is distributed in methylene chloride/saturated sodium bicarbonate solution. The methylene chloride phase is evaporated and the residue chromatographed over silica gel with toluene:glacial acetic acid:water = 10:10:1 as the eluent. After evaporation of the corresponding fractions and mixing with hexane under agitation, 48 mg (8.4% of theory) of 6-phenyl-4-methyl-β-carboline-3-carboxylic acid ethyl ester is obtained, mp 241°–242° C.

EXAMPLE 7

250 mg of 4-phenylindole in 1 ml of glacial acetic acid is added at room temperature to a solution of 1.1 g of 3-dimethylamino-2-(dimethylaminomethyleneamino)acrylic acid ethyl ester in 10 ml of glacial acetic acid, prepared at 0° C., and heated to 100° C. for 20 hours. After evaporation and repeated chromatography over silica gel with, in succession, methylene chloride:ethanol = 95:5; toluene:glacial acetic acid:water = 10:10:1; and methylene chloride:ethanol = 10:2, 21.4 mg of 5-phenyl-β-carboline-3-carboxylic acid ethyl ester is obtained.

The following compounds are produced analogously:

6-isopropyl-β-carboline-3-carboxylic acid ethyl ester, mp 222°–224° C.; and 5-benzyl-β-carboline-3-carboxylic acid ethyl ester.

EXAMPLE 8

260 mg of 6-benzoyl-4-methyl-β-carboline-3-carboxylic acid ethyl ester is hydrogenated in 36 ml of absolute ethanol with 2 ml of glacial acetic acid and 100 mg of palladium black for 2 hours at 10 bar hydrogen pressure at 40°–45° C. After separation of the catalyst, the reaction mixture is evaporated. The residue is chromatographed over silica gel, first with toluene:glacial acetic acid:water = 10:10:1 and then with toluene:ethanol:water = 80:20:1, thus obtaining 27 mg (11%) of 6-benzyl-4-methyl-β-carboline-3-carboxylic acid ethyl ester.

EXAMPLE 9

1.2 g of aluminum trichloride is added to a suspension of 500 mg of 4-methyl-β-carboline-3-carboxylic acid ethyl ester in 15 ml of tert-butyl chloride. The mixture is stirred for 2 hours at room temperature and thereafter combined with 50 ml of pentane. The supernatant solution is removed by decanting, and the precipitate is combined with 10 ml of ethanol and 30 ml of water. After setting the pH at 3, the mixture is extracted repeatedly with ether. The collected organic phases are dried, filtered, and concentrated. Recrystallization from ether yields 250 mg of 6-tert-butyl-4-methyl-β-carboline-3-carboxylic acid ethyl ester, mp 201°–203° C. From the mother liquor, 100 mg of 6,8-di-tert-butyl-4-methyl-β-carboline-3-carboxylic acid ethyl ester can be isolated, mp 260°–263° C.

6-tert-Butyl-β-carboline-3-carboxylic acid ethyl ester, mp 264°–269° C., is prepared analogously.

EXAMPLE 10

Under argon, 2.80 g (13.5 mmol) of 4-benzylindole is refluxed for 15 hours with 7.48 g (18 mmol) of a 50% strength solution of 4-methoxy-3-hydroxy-2-nitrobutyric acid ethyl ester in 84 ml of toluene with 8.3 ml of glacial acetic acid. After cooling, the reaction mixture is diluted with ethyl acetate and washed with water. The organic phase is dried, filtered, and concentrated, and the residue is chromatographed over silica gel with methylene chloride as the eluent, thus producing 4.7 g (87%) of 3-(4-benzylindol-3-yl)-2-nitro-5-oxahexanoic acid ethyl ester, which latter is hydrogenated in 50 ml of ethanol with 4.7 g of Raney nickel B 115-Z under normal pressure and at room temperature. After separation of the catalyst and evaporation, the product is chromatographed over silica gel with methylene chloride:ethanol=10:1, thus obtaining 1.16 g (24%) of 2-amino-3-(4-benzylindol-3-yl)-5-oxahexanoic acid ethyl ester; this product is combined with 349 mg of glyoxylic acid hydrate in 4 ml of ethyl acetate and 4 ml of water, adjusted to pH 4 with 10% potassium carbonate solution, and stirred overnight at room temperature. After the ethyl acetate has been removed by distillation, the product is diluted with water, extracted with methylene chloride, and the organic phase is dried, filtered, and concentrated, thus obtaining 1.7 g of a crude product which, without further purification, is refluxed in 40 ml of xylene for 5 hours. After concentration, the mixture is taken up in 40 ml of dimethyl sulfoxide, combined with 200 mg of sulfur, and heated for 75 minutes to 140° C. After the dimethyl sulfoxide has been removed by distillation, the mixture is chromatographed twice over silica gel, first with methylene chloride:ethanol=10:1 and then again with hexane:acetone=1:1, yielding 45 mg of 5-benzyl-4-methoxymethyl-β-carboline-3-carboxylic acid ethyl ester, mp 160°–168° C.

The following compounds are prepared in the same way:

6-isopropyl-4-methyl-β-carboline-3-carboxylic acid ethyl ester;

5-isopropyl-4-methyl-β-carboline-3-carboxylic acid ethyl ester;

5-benzyl-4-methyl-β-carboline-3-carboxylic acid ethyl ester; and 5-phenyl-4-methyl-β-carboline-3-carboxylic acid ethyl ester.

EXAMPLE 11

Under argon, 720 mg (2 mmol) of 6-iodo-4-methyl-β-carboline-3-carboxylic acid ethyl ester is heated in a pressure vessel with 202 mg (2.4 mmol) of sodium bicarbonate, 75 mg (0.42 mmol) of palladium dichloride, and 705 mg (8 mmol) of butenediol in 10 ml of N-methylpyrrolidone for 2 hours to 150° C. After filtration and concentration, the mixture is distributed in ethyl acetate/water. The aqueous phase is extracted twice with ethyl acetate, the combined organic phases are dried, filtered, and concentrated. The residue is chromatographed over silica gel with toluene:ethanol=80:40 as the eluent. Recrystallization of the corresponding fractions from ethyl acetate/diisopropyl ether yields 185 mg (26% of theory) of 6-(2-hydroxytetrahydrofuran-4-yl)-4-methyl-β-carboline-3-carboxylic acid ethyl ester, mp 177°–180° C.

EXAMPLE 12

100 mg (0.29 mmol) of 6-(2-hydroxytetrahydrofuran-4-yl)-4-methyl-β-carboline-3-carboxylic acid ethyl ester is refluxed in 5 ml of toluene with 10 mg of p-toluenesulfonic acid and 52 mg (0.35 mmol) of triethyl orthoformate for 1.5 hours. After concentration, the mixture is chromatographed over silica gel with toluene:glacial acetic acid:water=10:10:1 thus obtaining 29 mg (27% of theory) of 6-(2-ethoxytetrahydrofuran-4-yl)-4-methyl-β-carboline-3-carboxylic acid ethyl ester as an oil.

EXAMPLE 13

In a pressure vessel, 1.08 g (3 mmol) of 6-iodo-4-methyl-β-carboline-3-carboxylic acid ethyl ester is heated to 140° C. for 3 hours with 72 mg (0.06 mmol) of palladium(II) acetate, 0.48 ml (3.6 mmol) of triethylamine, and 432 mg (4.5 mmol) of 2-cyclohexen-1-one in 10 ml of absolute dimethylformamide. After concentration, the mixture is chromatographed over silica gel with methylene chloride:ethanol=10:2. After recrystallization of the combined polar fractions from methylene chloride/cyclohexane, 75 mg (6.7% of theory) of 6-(1-oxo-2-cyclohexen-3-yl)-4-methyl-β-carboline-3-carboxylic acid ethyl ester is obtained, mp 245°–248° C. After recrystallization from ethyl acetate, the combined nonpolar fractions, which are chromatographed twice over silica gel with toluene:glacial acetic acid:water=10:10:1, yield 60 mg (5.8% of theory) of 6-(1-oxocyclohex-3-yl)-4-methyl-β-carboline-3-carboxylic acid ethyl ester, mp 182°–189° C.

Analogously, 6-iodo-4-methyl-β-carboline-3-carboxylic acid ethyl ester and 2-methyl-2-propen-1-ol yield the 6-(2-formylpropyl)-4-methyl-β-carboline-3-carboxylic acid ethyl ester, mp 184°–187° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A substituted β-carboline of the formula

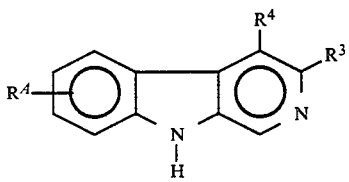

wherein $R^3$ is (a) oxadiazolyl of the formula

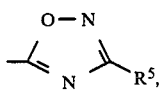

wherein $R^5$ is lower alkyl of up to 3 carbon atoms, or (b)

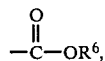

wherein $R^6$ is hydrogen or lower alkyl of up to 3 carbon atoms;

$R^4$ is hydrogen, lower alkyl of up to 3 carbon atoms, or —CH$_2$OR$^9$, wherein $R^9$ is lower alkyl of up to 3 carbon atoms;

$R^4$ is (a) phenyl, (b) alkenyl, cycloalkyl or cycloalkenyl each of 2–10 carbon atoms, (c) one of said (b) groups substituted by formyl, OH, O-alkyl of up 3 carbon atoms or phenyl, wherein when $R^4$ is cycloalkyl or cycloalkenyl, a CH$_2$-group can be replaced by tetrahydrofuranyl or a cyclohexanone group.

2. A compound of claim 1 wherein $R^3$ is

alkyl.

3. A compound of claim 1 wherein $R^3$ is

4. A compound of claim 1 wherein $R^3$ is oxadiazolyl.

5. A compound of claim 1 wherein $R^4$ is not H.

6. A compound of claim 1 wherein $R^4$ is phenyl, alkenyl, cycloalkyl or cycloalkenyl.

7. A compound of claim 1 wherein $R^4$ is in the 6-position.

8. 6-Cyclohexyl-4-methyl-β-carboline-3-carboxylic acid ethyl ester, a compound of claim 1.

9. 6-tert-Butyl-4-methyl-β-carboline-3-carboxylic acid ethyl ester.

10. 6-Phenethyl-4-methyl-β-carboline-3-carboxylic acid ethyl ester, a compound of claim 1.

11. 6-(1-Cycloocten-1-yl)-4-methyl-β-carboline-3-carboxylic acid ethyl ester, a compound of claim 1.

12. 6-(1- and 2-Cyclohexen-4-yl)-4-methyl-β-carboline-3-carboxylic acid ethyl ester, a compound of claim 1.

13. 6-Isopropyl-β-carboline-3-carboxylic acid ethyl ester, a compound of claim 1.

14. 5-Benzyl-4-methoxymethyl-β-carboline-3-carboxylic acid ethyl ester, a compound of claim 1.

15. 6-(1-Oxocyclohex-3-yl)-4-methyl-β-carboline-3-carboxylic acid ethyl ester, a compound of claim 1.

16. A pharmaceutical composition comprising an anticonvulsant or anxiolytic effective amount of a compound of claim 1 and a pharmacologically acceptable carrier.

17. A pharmaceutical composition of claim 16 wherein said amount is 0.05–1 mg.

18. A method of treating an indication in a patient which can be treated by an agent having an affinity to benzodiazepine receptors comprising administering to the patient an anxialytically or anticonvulsant effective amount of a compound of claim 1.

19. A compound of claim 1 wherein $R^4$ is cycloalkyl or cycloalkenyl.

20. A compound of claim 1 wherein $R^4$ is alkenyl.

21. A compound of claim 1 wherein $R^4$ is phenyl.

22. A compound of claim 1 wherein $R^4$ is cyclopenyl, cycolhexyl, cycloheptyl, cyclooctyl, 1,3-butadienyl, 1-cyclohexenyl, 4-cycloheptenyl, 1-cyclooctenyl, 2,3-dimethyl-1,3-butadienyl, 3-methyl-1,3-butadienyl, cyclohexyvinyl, phenethyl, or 2-cyclohexylethyl.

23. A method of achieving a muscle relaxant, antiepileptic, sedative, hypnotic or tranquilizing effect in a patient comprising administering an effective amount of a compound of claim 1.

24. A method of treating anxiety or epilepsy in a patient comprising administering an anxiolytically effective or antioconvulsant effective amount, respectively, of a compound of claim 1.

25. A substituted β-carboline of the formula

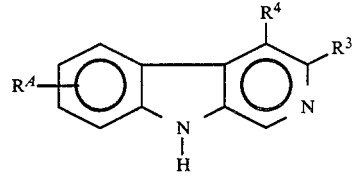

wherein $R^3$ is (a) oxadiazolyl of the formula

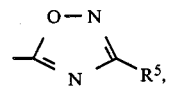

wherein $R^5$ is lower alkyl of up to 3 carbon atoms, or (b)

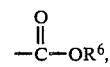

wherein $R^6$ is hydrogen or lower alkyl of up to 3 carbon atoms;

$R^4$ is hydrogen, lower alkyl of up to 3 carbon atoms, or —CH$_2$OR$^9$, wherein $R^9$ is lower alkyl of up to 3 carbon atoms;

$R^4$ is alkyl substituted by oxo, formyl or phenyl.

26. A substituted β-carboline of the formula

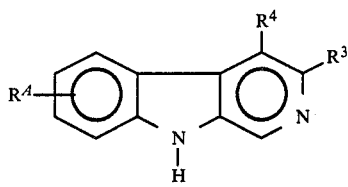

wherein

R³ is (a) oxadiazolyl of the formula

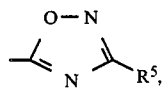

wherein R⁵ is lower alkyl of up to 3 carbon atoms, or (b)

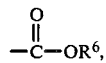

wherein $R^6$ is hydrogen or lower alkyl of up to 3 carbon atoms;

$R^4$ is hydrogen, lower alkyl of up to 3 carbon atoms, or —$CH_2OR^9$, wherein $R^9$ is lower alkyl of up to 3 carbon atoms;

$R^A$ is alkyl of 2–10 carbon atoms or alkyl of 2–10 carbon atoms substituted by OH or O-alkyl of up to 3 carbon atoms.

27. A pharmaceutical composition comprising an anticonvulsant or anxiolytic effective amount of a compound of claim 25 and a pharmacologically acceptable carrier.

28. A pharmaceutical composition comprising an anticonvulsant or anxiolytic effective amount of a compound of claim 26 and a pharmacologically acceptable carrier.

29. A method of treating an indication in a patient which can be treated by an agent having an affinity to benzodiazepine receptors comprising administering to the patient an anxiolytically or anticonvulsant effective amount of a compound of claim 25.

30. A method of treating an indication in a patient which can be treated by an agent having an affinity to banzodiazepine receptors comprising administering to the patient an anxiolytically or anticonvulsant effective amount of a compound of claim 26.

* * * * *